United States Patent [19]

Theuwis

[11] 4,401,389

[45] Aug. 30, 1983

[54] MEASURING PROBE FOR TAKING A SAMPLE FROM A METAL BATH AND FOR MEASURING THE BATH TEMPERATURES

[75] Inventor: Alfons L. M. C. Theuwis, Zonhoven, Belgium

[73] Assignee: Electro-Nite Co., Philadelphia, Pa.

[21] Appl. No.: 339,806

[22] Filed: Jan. 15, 1982

[30] Foreign Application Priority Data

Jan. 24, 1981 [DE] Fed. Rep. of Germany ... 8101697[U]

[51] Int. Cl.³ .............................................. G01N 1/12
[52] U.S. Cl. ................................ 374/140; 73/864.55; 374/157

[58] Field of Search .......... 73/61 LM, 864.53, 864.54, 73/864.55, 864.56, 864.57, 864.58, 864.59; 374/140, 157

[56] References Cited

U.S. PATENT DOCUMENTS

| | | | |
|---|---|---|---|
| 3,455,164 | 7/1969 | Boyle | 73/864.59 |
| 3,753,372 | 8/1973 | Collins | 73/864.56 |
| 3,950,992 | 4/1976 | Hance | 73/864.55 |
| 4,211,117 | 7/1980 | Cure | 73/864.55 |

*Primary Examiner*—S. Clement Swisher
*Attorney, Agent, or Firm*—Seidel, Gonda & Goldhammer

[57] ABSTRACT

The body of a probe adapted to be immersed in molten metal has a sensor for measuring temperature and a container for taking a sample of the molten metal.

9 Claims, 7 Drawing Figures

MEASURING PROBE FOR TAKING A SAMPLE FROM A METAL BATH AND FOR MEASURING THE BATH TEMPERATURES

This innovation relates to a measuring probe for simultaneously taking a sample from a molten metal bath and for measuring the bath temperature, said probe being adapted to be inserted into the end of a lance and consisting of a sample container and a measuring device disposed on a common headpiece consisting of a cylindrical body surmounted by a collar and intended partially to receive the sample container, said headpiece being inserted into one end of a connecting tube in whose other end there is secured a cylindrical plug containing a coupling member and formed with longitudinal grooves on the outside, said plug being adapted to close the connecting tube and its other end having a cylindrical projection to receive an intermediate tube. A protective tube is pushed on to the two tubes and the plug until it contacts the collar of the cylindrical body, the inside diameter of said protective tube being substantially equivalent to the outside diameters of the plug and of the headpiece.

The object of the invention is to improve the assembly and construction of a known measuring probe of this kind and, more particularly, so construct the probe headpiece that the temperature measuring device and, if required, an additional device of known construction for determining the oxygen content of the molten metal melt, can be secured with simple means.

Starting from a measuring probe of the type described hereinbefore, according to the invention, the cylindrical member forming the headpiece has at least one other bore in addition to a central bore to receive the supply tube of the two-part sample container, said additional bore terminating at a cylindrical member end portion which is situated opposite the collar and which has a smaller diameter than the middle portion of said cylindrical member and is formed with a continuous slot of a size equal to the thickness of the sample container, and the wall of the middle part of the cylindrical member is formed with a recess in the region of the bottom end of the bore, said recess opening the bore out to the outer wall.

According to the invention, the cylindrical member forming the headpiece may have two bores disposed on either side of the middle bore and preferably having a rectangular cross-section.

According to another feature of the invention, a mount, preferably made from plastics, is inserted into one of the bores disposed adjacent the middle bore, said mount being adapted to the cross-section of the bore and the temperature measuring device being secured thereon. In another embodiment of the invention, a measuring probe of known construction for determining the oxygen content of the melt is additionally disposed in the second bore and is also secured on a preferably plastics mount. The two mounts with the measuring devices secured thereto and the connecting leads fitted thereon can readily be introduced from above into the corresponding bores and are fixed in their position because the mounts are adapted to the cross-section of the bores and bear on the base of the bore in the region of the recesses. According to the invention, the leads providing the electrical connections are taken through the recesses in the middle part of the cylindrical member and along the outer surface and the connecting tube to the corresponding contacts of the coupling member.

Advantageously, the region of the surface of the cylindrical member surrounding the middle opening is provided with a recess which extends as far as the bores disposed adjacent the same. After the insertion of the measuring device or devices this recess can be filled with refractory cement or another suitable material.

The sample is usually held by relatively thin two-part sample containers which can be inserted into the cylindrical member. To this end, the slot provided in the end portion of the cylindrical member continues as far as the middle part thereof.

According to the invention, however, it is possible to use a sample container of greater thickness which extends into the cylindrical hollow member only in the region of the slot, which is made in a corresponding width, said sample container being provided with a thermocouple which extends through the middle transverse axis of the container and which serves to record the cooling curve of the sample taken. Three measurements can thus be carried out simultaneously.

The measuring probe according to this invention is of very simple construction. It can be assembled without great difficulty by fitting a few parts together and be adapted to the required purpose of use.

Exemplified embodiments of the invention are illustrated in the drawing wherein.

Figure 1:
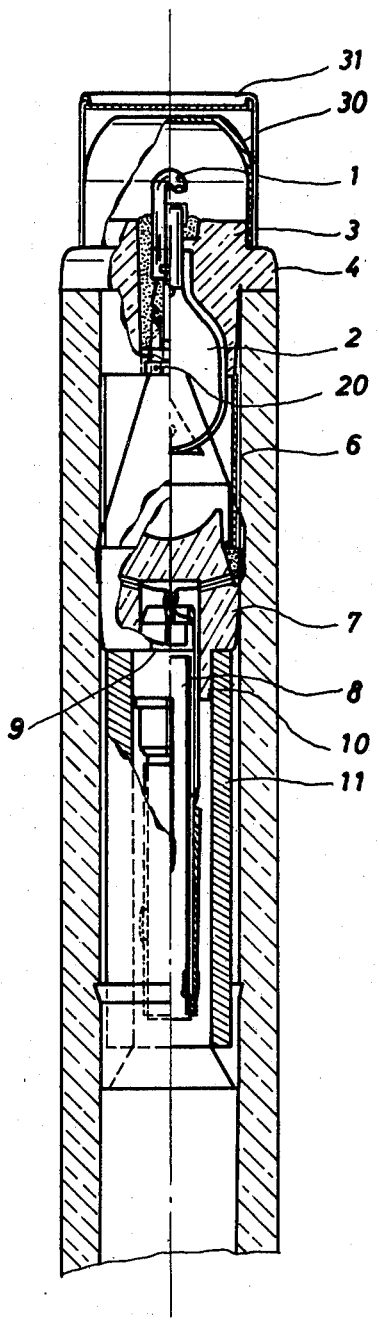
FIGS. 1 and 2 are side elevations in partial section showing a measuring probe from two 90°-offset directions.
Figure 2:
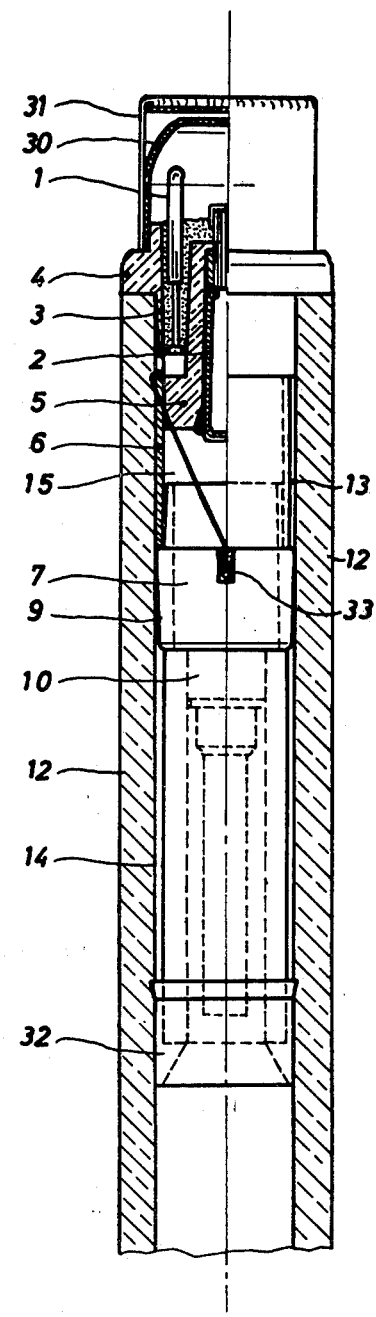

The measuring probe shown in FIGS. 1 and 2 enables a sample to be taken from a molten metal bath and the temperature of the bath to be measured at the same time. To this end, the probe contains a thermocouple 1 and a sample container 2 disposed on a common headpiece 3. The latter consists of a cylindrical member surmounted by a collar 4 and intended partially to receive the sample container 2, which is inserted from below into a slot formed in the interior of the headpiece and of a size adapted to the thickness of the sample container. An end portion 5 of the headpiece 3 is inserted into one end of a connecting tube 6, in the other end of which a cylindrical plug 7 is secured to close the connecting tube. Plug 7 contains a coupling member 8 constructed in known manner and having the necessary connections and contacts, and its outside is provided with two diametrically opposite longitudinal grooves 9. It also contains a cylindrical projection 10 to receive an intermediate tube 11, the outside diameter of which is somewhat smaller than that of the plug 7. Connecting tube 6, plug 7 and intermediate tube 11 are surrounded by a protective tube 12 which is shown only in FIG. 2 and which is pushed on until it contacts the collar 4 of the headpiece 3. The inside diameter is approximately the same as the outside diameter of the plug 7 and of the headpiece 3, so that annular spaces 13 and 14 are left between the outer surfaces of the tubes 6 and 11 and the inner surface of the protective tube 12, said spaces being interconnected via the longitudinal grooves 9 which are of a depth that such that they also connect the interior 15 of the tube 6 to the annular space 14 so that gases forming in the interior of the tube 6 can be discharged via the grooves 9 and the annular space 14.

Figure 3:
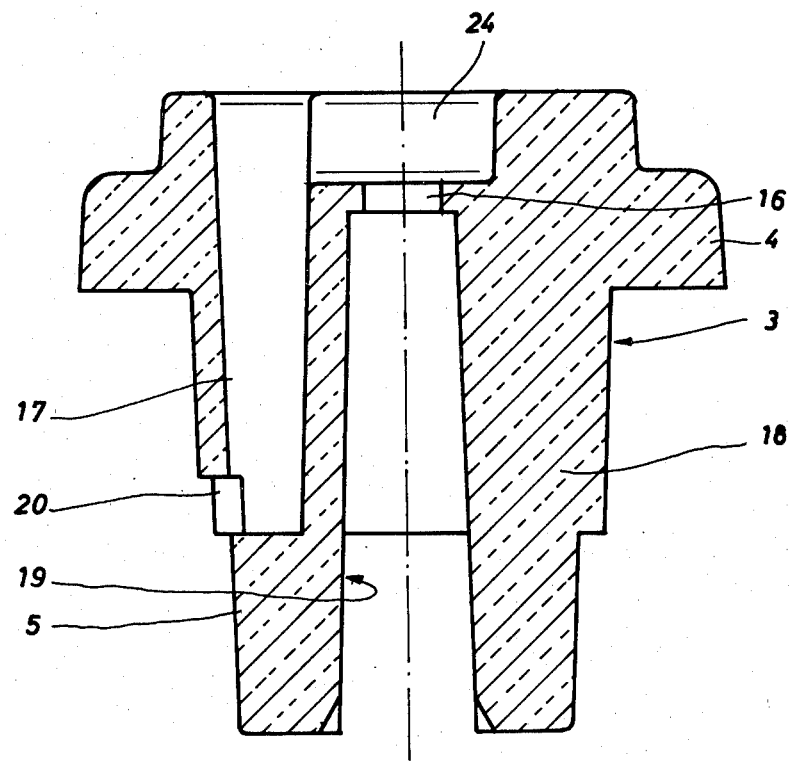
FIG. 3 is a vertical section through a headpiece.
Figure 4:
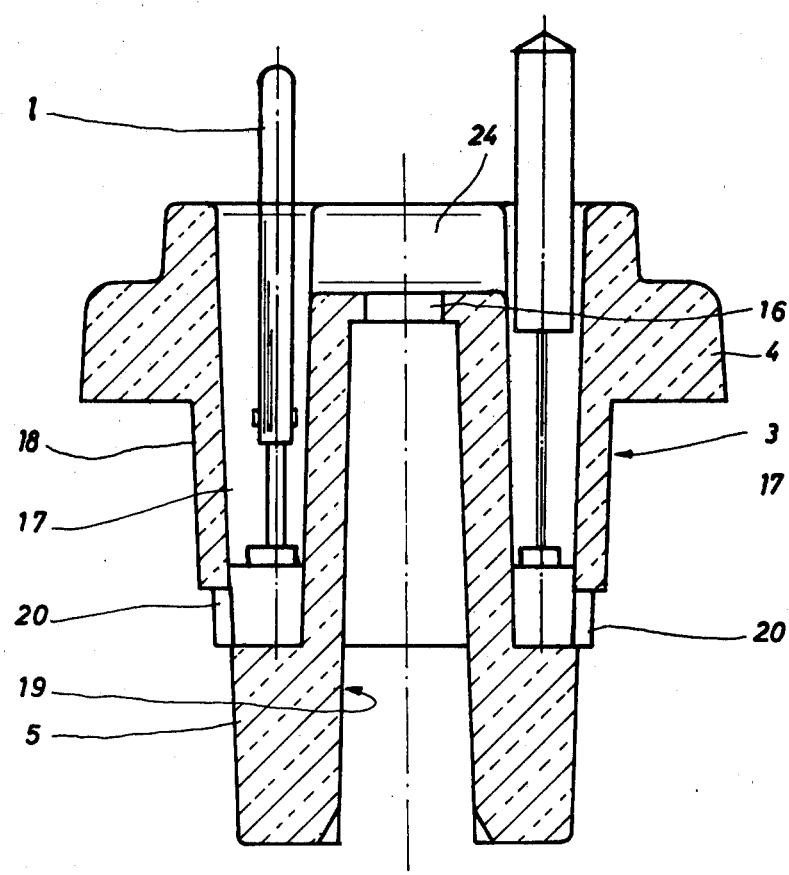
FIG. 4 is a similar view of another embodiment of a headpiece with the measuring devices fitted.

FIG. 3 shows the headpiece 3 to an enlarged scale. It conventionally contains a central bore 16 to receive the supply tube of the two-part sample container and another bore 17 disposed adjacent it and terminating at the end portion 5 opposite the collar, said end portion having a smaller diameter than the middle portion 18 of the cylindrical member and having a middle continuous slot 19 of a thickness equal to the sample container, said slot continuing in the form of a cavity into the middle part of the headpiece. Thewall of the middle part of the cylindrical member or headpiece 3 is formed with a recess 20 near the bottom end of the bore 17, said recess opening the bore out to the outer wall. In another embodiment of the invention shown in FIG. 4, the cylindrical member has two diametrically opposite bores 17 which are disposed on either side of the central bore 16, one of these bores being adapted to receive a thermocouple and the other a measuring probe 29 of known type for determining the oxygen content.

Figure 5:
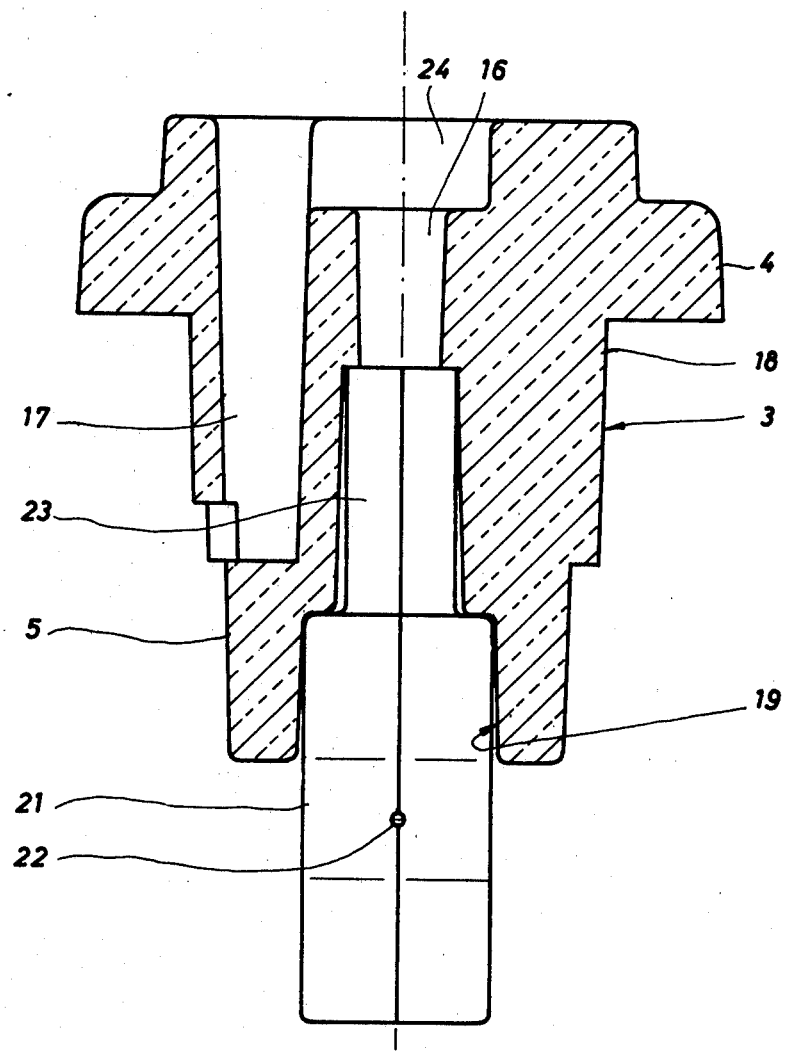
FIG. 5 illustrates a headpiece having an enlarged slot for partial insertion of a sample container provided with a thermocouple.

A third embodiment is shown in FIG. 5, in which the slot 19 is wider in the bottom region of the headpiece 3 and serves to receive a sample container 21 of corresponding thickness, which is provided with a thermocouple disposed in a quartz tube fitted through opposite bores 22 in the walls of the sample container and extending through the same. In this way it is possible to record cooling curve for the metal solidifying in the sample container. Of course the embodiment shown in FIG. 5 may also contain two bores 17. The sample container 21 is connected to the top surface of the headpiece 3 via an inlet tube 23 and the correspondingly lengthened middle bore 16. It has been found advantageous for that zone of the surface of the cylindrical member which surrounds the central opening to be formed with a recess 24 extending as far as the bore or bores 17.

Figures 6, 7:
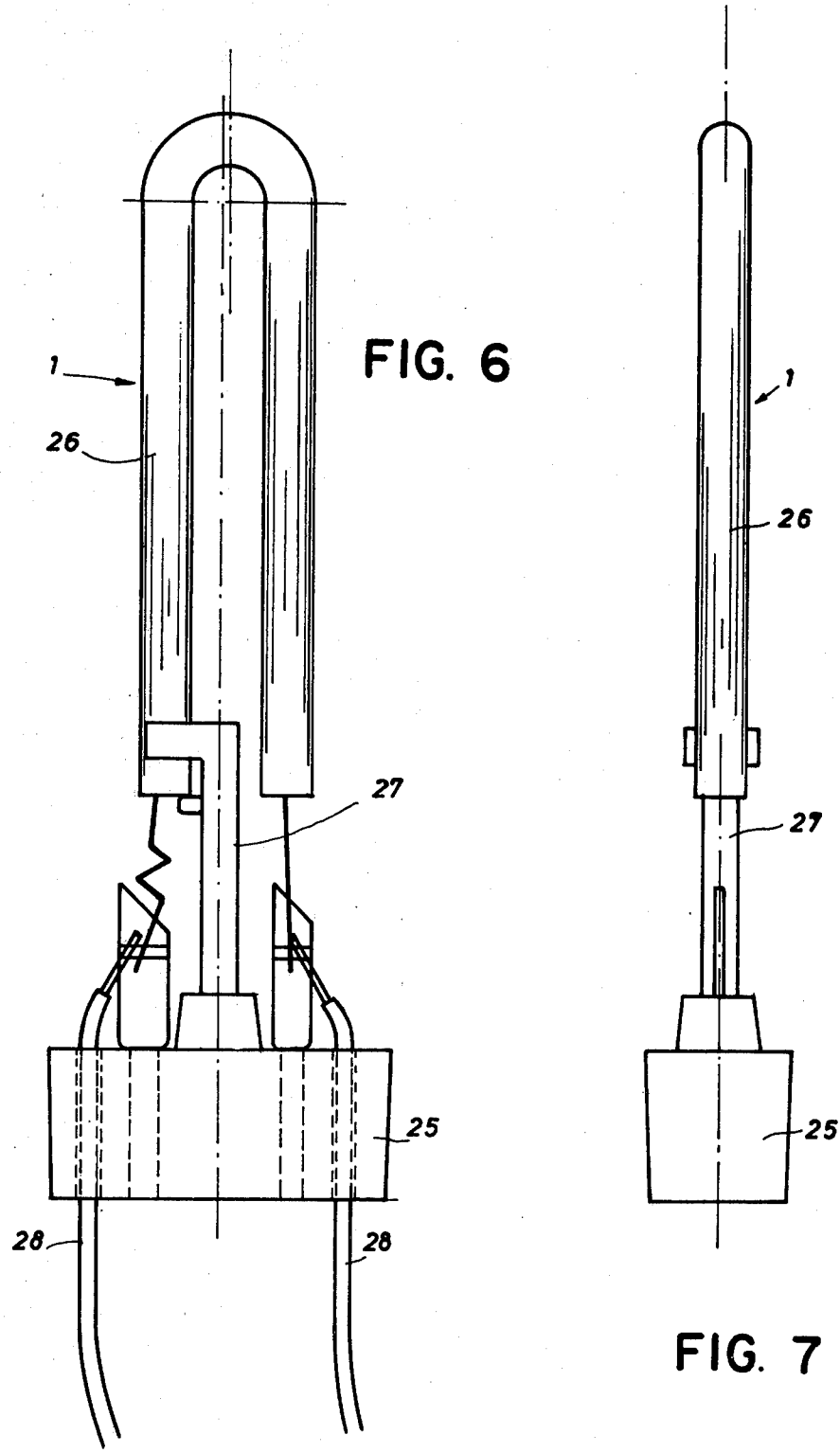
FIG. 6 is a side elevation.
FIG. 7 is a front elevation of a mount with a thermocouple secured thereto.

FIGS. 6 and 7 show a plastics mount 25 fitted into one of the bores 17. In a preferred embodiment of the invention the bores have a substantially rectangular cross-section to which the mount 25 is adapted, so that a thermocouple 1 secured on the mount and disposed in the U-shaped quartz tube 26 fits tightly in the bore. Reference 27 is a support for holding the quartz tube 26, and this may also consist of plastics like the base of the mount 25. The leads 28 to the thermocouple are taken out of recess 20 as shown in FIG. 1, extend along the outside of the connecting tube 6, and are taken to the coupling member connections via a recess 33 in the cylindrical plug 7.

The measuring probe is conventionally provided with a metal cap 30 and a cardboard protective cap 31 disposed thereabove, said cap 31 covering the measuring devices taken out of the headpiece.

Reference 32 denotes a spacer ring which is disposed at the other end of the measuring probe, bears against the inner wall of the protective tube 12, and is also provided with longitudinally extending grooves through which gas collecting in the annular space 14 can escape.

The measuring probe allows very simple and advantageous assembly since the measuring devices and the sample container can first be inserted into the headpiece 3, the remaining cavities formed by the bores and the recess 24 being conventionally filled with refractory cement or some other suitable compound. Connecting tube 6 is then fitted, the cylindrical plug being inserted into its other end. The electrical connections can be made to this pre-assembled, very handy and stable part of the measuring probe, and then the intermediate tube 11 and the protective tube can be fitted.

I claim:

1. A measuring probe for simultaneously taking a sample from a molten metal bath and for measuring a parameter of the bath comprising a sample container and a device for measuring a parameter of a molten metal bath each disposed on a common head piece, said head piece including a cylindrical body having a collar at one end, said body partially receiving a sample container, said head piece having its other end inserted into one end of a connecting tube, the other end of the connecting tube being secured to and closed by one end of a cylindrical plug, said plug having at least one longitudinally extending peripheral gas-vent groove, the other end of said plug having a cylindrical projection telescoped with respect to one end of an intermediate tube, said connecting tube and said intermediate tube and the plug each being surrounded by a protective tube telescoped onto said head piece and in contact with said collar, the inside diameter of said protective tube being substantially equivalent to the outside diameter of the plug and said cylindrical body, the interior of said connecting tube being vented for escape of gases to the chamber between said protective tube and said intermediate tube by way of said groove, said cylindrical body having a central bore and at least one other bore generally parallel thereto, said central bore at said one end of the body receiving a supply tube for said sample container, said additional bore being shorter than the length of said body and having a radially disposed exit port at theouter perphery of said body, said cylindrical body having a slot coextensive with said central bore and receiving said sample container, an electrical contact device supported within said intermediate tube and electrically coupled to said measuring device, and a spacer at the other end of said intermediate tube, said spacer being provided with means to vent gases from said chamber.

2. A measuring probe according to claim 1, characterised in that the headpiece (3) is provided with two bores (17) disposed on either side of the middle bore (16).

3. A measuring probe according to claims 1 and 2, characterised in that the bores (17) have a substantially rectangular cross-section.

4. A measuring probe according to claims 2, 3 and 1, characterised in that a mount (25), preferably made from plastics, is inserted into one of the bores (17) disposed adjacent the middle bore, said mount being adapted to the cross-section of the bore and the temperature measuring device (1) being secured thereon.

5. A measuring probe according to claims 2-4 and 1, characterised in that a measuring probe of known construction for determining the oxygen content of the melt is disposed in the second bore (17) and is also secured on a preferably plastics mount (25) whose cross-section is adapted to that of the bore.

6. A measuring probe according to claims 4 and 5, characterised in that the leads (28) are taken to the corresponding contacts of the coupling member (7) through the recesses (20) at the bottom end of the bore.

7. A measuring probe according to claims 2–6 and 1, characterised in that a region of the surface of the headpiece (3) surrounding the middle opening (16) is provided with a recess (24) which extends as far as the bores (17) disposed adjacent the same.

8. A measuring probe according to claims 2–7 and 1, characterised in that the sample holder (21) is inserted into the headpiece (3) only in the region of a widened portion of the slot (19) and is provided with a thermocouple which extends through the central transverse axis of the sample container and which is fitted through appropriately disposed bores (22) in the sample container (21), the thickness of which is adapted to the widened portion of the slot (19).

9. A measuring probe in accordance with claim 1 wherein the other end of said body terminates in a portion which is smaller in diameter than a middle portion thereof, each of said middle portion and said smaller diameter portion having a shoulder along said central bore for contact with said sample container.

* * * * *